(12) United States Patent
Wu et al.

(10) Patent No.: US 11,116,627 B2
(45) Date of Patent: Sep. 14, 2021

(54) INTRAOCULAR LENS INJECTOR

(71) Applicant: Alcon Inc., Fribourg (CH)

(72) Inventors: Yinghui Wu, Cedar Hill, TX (US);
Douglas Brent Wensrich, Bedford, TX (US); Len Takudzwa Magara, Pretoria (ZA)

(73) Assignee: Alcon Inc.

( * ) Notice: Subject to any disclaimer, the term of this patent is extended or adjusted under 35 U.S.C. 154(b) by 155 days.

(21) Appl. No.: 16/507,137

(22) Filed: Jul. 10, 2019

(65) Prior Publication Data

US 2020/0015956 A1 Jan. 16, 2020

Related U.S. Application Data

(60) Provisional application No. 62/696,065, filed on Jul. 10, 2018.

(51) Int. Cl.
*A61F 2/16* (2006.01)

(52) U.S. Cl.
CPC ............ *A61F 2/167* (2013.01); *A61F 2/1678* (2013.01)

(58) Field of Classification Search
CPC ...... A61F 2/167; A61F 2/1678; A61F 2/1662; A61F 2/1667; A61F 2/1672; A61F 2/1675; A61F 2/1691; A61F 2002/1681; A61F 2002/1682; A61F 2002/16903; A61F 2002/16905; A61F 2002/169051; A61F 2002/169052; A61F 2002/169053
See application file for complete search history.

(56) References Cited

U.S. PATENT DOCUMENTS

2013/0338676 A1* 12/2013 Marunaka ............... A61F 2/167
                                                              606/107
2016/0256316 A1* 9/2016 Van Noy ............. A61F 9/00736

FOREIGN PATENT DOCUMENTS

| EP | 1967161 A1 | 9/2008 |
|----|------------|--------|
| EP | 2491902 A1 | 8/2012 |
| WO | 2015112146 A1 | 7/2015 |

* cited by examiner

*Primary Examiner* — Erich G Herbermann

(57) ABSTRACT

Intraocular lens injectors described herein may include a symmetrical arranged storage compartment, nozzle passage, and plunger tip in order to symmetrically fold and provide symmetrical loading to an intraocular lens during advancement and delivery so as to avoid rotation of the intraocular lens about longitudinal, vertical, and/or lateral axes during advancement and/or delivery of the intraocular lens.

14 Claims, 11 Drawing Sheets

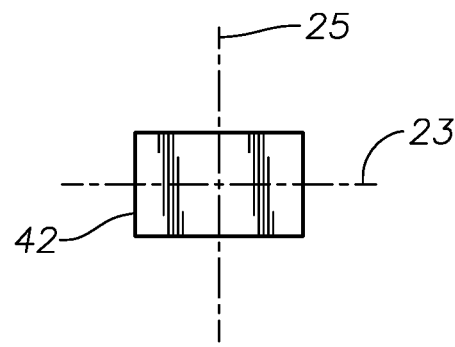
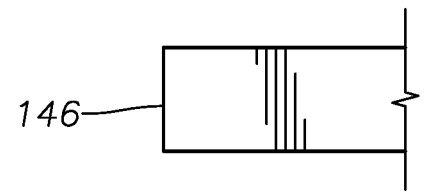
FIG. 17  FIG. 18
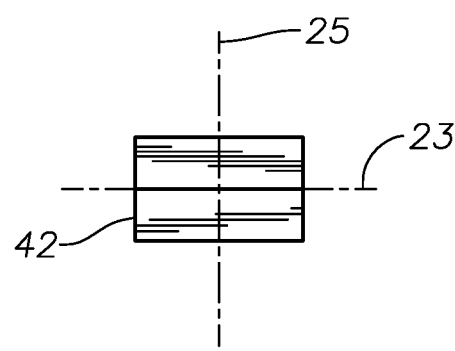
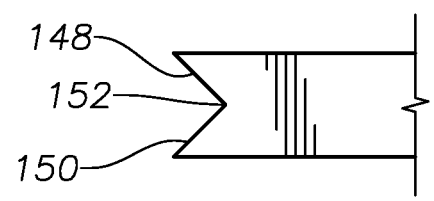
FIG. 19  FIG. 20
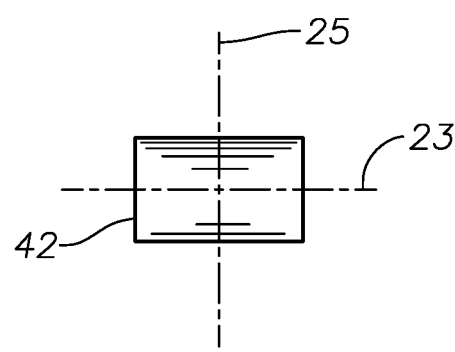
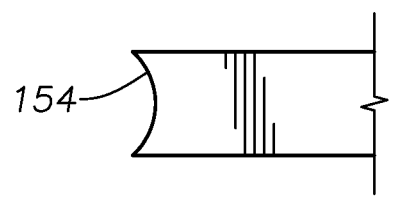
FIG. 21  FIG. 22

INTRAOCULAR LENS INJECTOR

CROSS-REFERENCE TO RELATED APPLICATIONS

This application claims the benefit of U.S. Provisional Application No. 62/696,065, filed Jul. 10, 2018, the entire contents of which are incorporated herein by reference.

TECHNICAL FIELD

The present disclosure relates to systems, apparatuses, and methods for intraocular lens injectors.

BACKGROUND

The human eye in its simplest terms functions to provide vision by transmitting and refracting light through a clear outer portion called the cornea, and further focusing the image by way of the lens onto the retina at the back of the eye. The quality of the focused image depends on many factors including the size, shape and length of the eye, and the shape and transparency of the cornea and lens. When trauma, age or disease cause the lens to become less transparent, vision deteriorates because of the diminished light which can be transmitted to the retina. This deficiency in the lens of the eye is medically known as a cataract. The treatment for this condition is surgical removal of the lens and implantation of an artificial intraocular lens ("IOL").

Many cataractous lenses are removed by a surgical technique called phacoemulsification. During this procedure, an opening is made in the anterior capsule and a thin phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by an artificial lens.

The IOL is injected into the eye through the same small incision used to remove the diseased lens. An IOL injector is used to deliver an IOL into the eye.

SUMMARY

According to one aspect, the disclosure describes an intraocular lens injector that may include a main body portion defining a central longitudinal axis, a storage portion disposed at a distal end of the main body portion, a nozzle disposed at a distal end of the storage portion, and a plunger received into the main body portion and slideable therein. The storage portion may include a compartment that includes a floor. The compartment may be adapted to store an intraocular lens prior to delivery, and the compartment may be shaped symmetrically about a plane extending through the central longitudinal axis and a vertical axis extending perpendicular to the floor of the compartment such that the compartment applies balanced loading to the intraocular lens relative to the plane. The nozzle may include an interior wall defining a passage, the interior wall and passage symmetrical about the plane; a distally extending distal tip; and an opening formed at the distal end of the distal tip, the opening in fluid communication with the passage. The plunger may include a plunger tip that is symmetrical about the plane.

The compartment comprises walls symmetrically disposed about the plane. The walls of the compartment and the wall of nozzle may define a continuous contour. The compartment may include a distal opening. The nozzle may include a proximal opening, and the distal opening and the proximal opening may correspond to each other. The wall of the compartment may converge such that the distal opening is narrower than a proximal portion of the compartment. The compartment may include walls symmetrically disposed about the plane. The compartment may include protuberances formed along the walls, and the protuberances may be adapted to contact an IOL disposed in the compartment at locations that are symmetrical about the plane. A door that may overlay the compartment. The door may include rails formed on an inner surface and symmetrically disposed relative to the plane. Each of the rails may include an inwardly converging portion that are symmetrically arranged relative to the plane. The plunger may include a plunger rod. The plunger tip may be disposed at a distal end of the plunger rod. The rails may converge to define a slot adapted to maintain a path of travel of the plunger rod.

A lens stop removably attachable to the door. The lens stop may include protrusions extending from a first surface adapted to abut an exterior surface of the door, opposite the interior surface of the door. The door may also include first apertures extending therethrough. The first apertures may be arranged symmetrically relative to the plane. The protrusions may extend through the first apertures formed in the door. The protrusions may be operable to symmetrically contact the intraocular lens disposed in the compartment and limit movement of the intraocular lens therein. The lens stop may also include an additional aperture. The additional aperture may be centrally located along the plane. The lens stop may also include a spout defining a passage, and the spout may be received into the additional aperture when the lens stop is attached to the door. The first protrusions may extend from the floor. The first protrusions may be arranged symmetrically relative to the plane. The protrusions may be operable to symmetrically contact the intraocular lens disposed in the compartment and limit movement of the intraocular lens therein. The first protrusions may be retractable. The nozzle may include a proximal portion. The proximal portion may include longitudinally extending sidewalls, and a cover. The cover and the longitudinally extending sidewalls may define a cavity. The cover and the longitudinally extending sidewalls may enclose the compartment. The cover may be fixedly attached to the nozzle. The storage portion may include longitudinally extending wall and rails extending from the longitudinally extending walls. The longitudinally extending walls of the proximal portion may include slots formed therein, and the rails may be received into the slot when the nozzle is coupled to the storage portion. The cover may include inner walls. Each of the longitudinally extending walls of the storage portion may be disposed between one of the longitudinally extending wall of the proximal portion and one of the inner walls of the cover when the storage compartment is coupled to the nozzle.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

FIGS. 17-22 show example plunger tips having symmetrical shaped ends.

DETAILED DESCRIPTION

Figure 1:
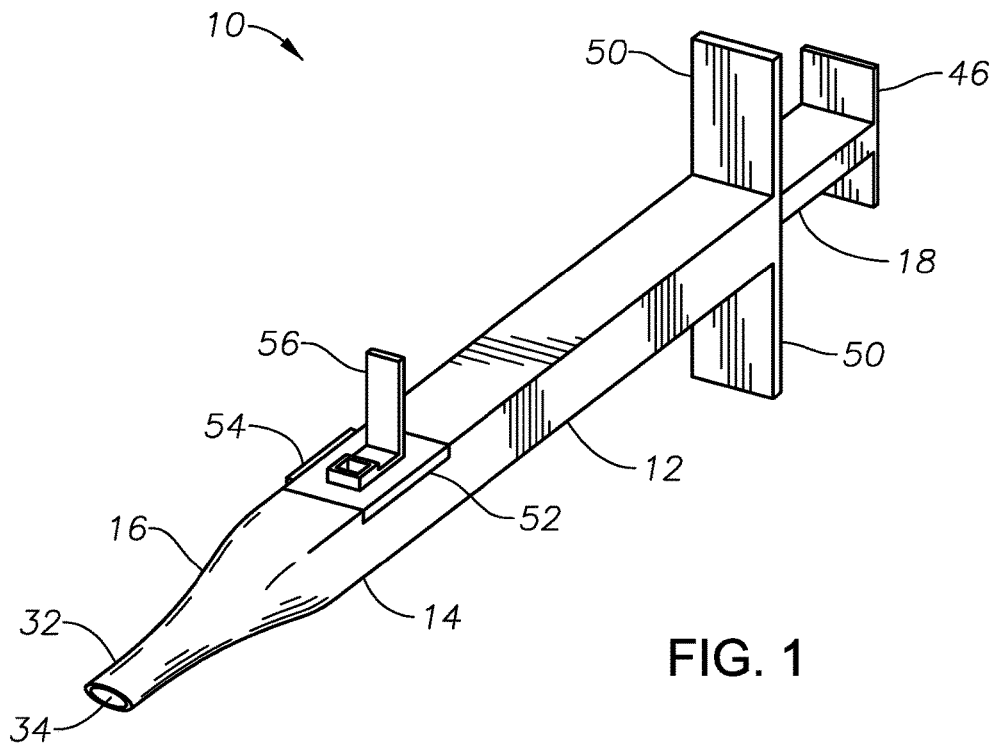
FIG. 1 is a perspective view of an example intraocular lens injector.

For the purposes of promoting an understanding of the principles of the present disclosure, reference will now be made to the implementations illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

The present disclosure relates to systems, apparatuses, and methods for delivering an IOL into an eye. Particularly, the present disclosure describes intraocular (IOL) injectors having symmetrically arranged nozzles, lens wells, and plunger tips for delivering an IOL or portion thereof into an eye and associated methods.

Figure 2:
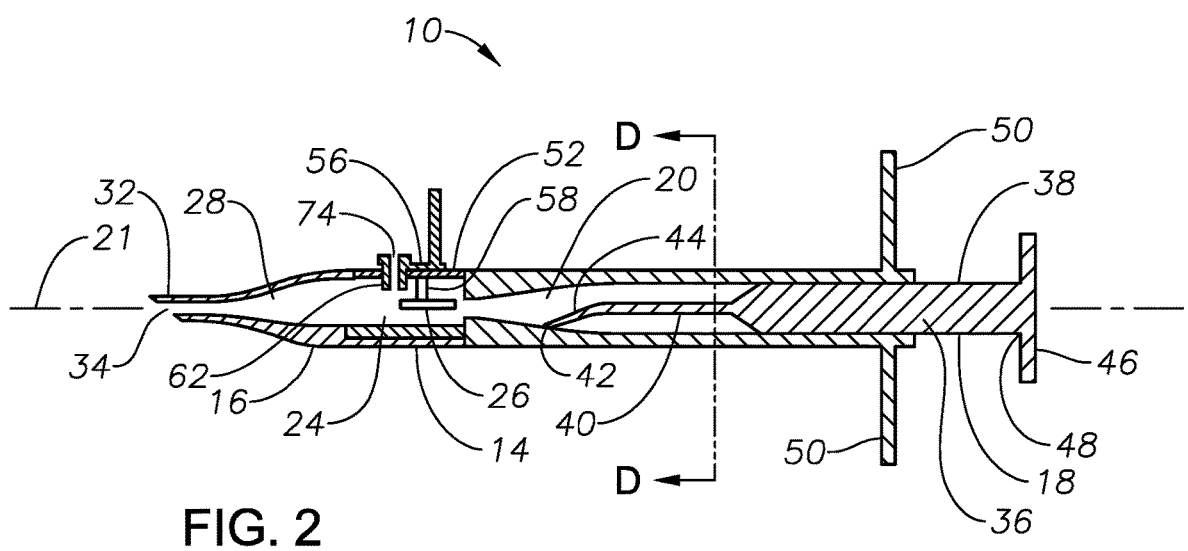
FIG. 2 shows a longitudinal cross-sectional view of the intraocular lens ("IOL") injector of FIG. 1.
Figure 23:
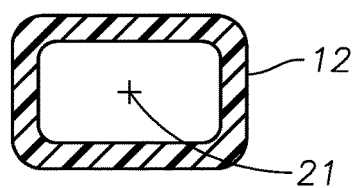
FIG. 23 is a cross-sectional view of the main body portion taken along line DD.

FIGS. 1 and 2 show an example IOL injector 10. The IOL injector 10 includes a main body portion 12, an IOL storage portion 14, a nozzle 16, and a plunger 18. The main body portion 12 defines a central passage 20 extending from a proximal end 22 of the main body portion 12. The central passage 20 defines a central longitudinal axis 21. In some implementations, the longitudinal axis 21 may extends through a center of a cross-section of the central passage 20, as shown in the transverse cross-sectional view taken along line DD in FIG. 23. The storage portion 14 defines a compartment 24 in which an IOL 26 is received. The nozzle 16 defines a passage 28 that narrows in cross-sectional size from a proximal end 30 of the nozzle 16 to a distal tip 32. The narrowing passage 28 operates to fold the IOL 26 as the IOL 26 is advanced therethrough, as described in more detail below. The passage 28 defines an opening 34 formed in the distal tip 32, though which the IOL 26 is expelled from the IOL injector 10, such as into an eye of a patent. The central passage 20, the compartment 24, and passage 28 are in fluid communications with each other.

The plunger 18 is received into the central passage 20 through an opening 36 formed at the proximal end 22 of the main body portion 12. The plunger 18 includes a plunger base 38, a plunger rod 40 extending distally from the plunger base 38, and a plunger tip 42 formed at a distal end 44 of the plunger rod 40. The plunger 18 also includes a flange 46 at a distal end 48, and the main body portion 12 includes protrusions 50 extending from the proximal end 22. As shown in the illustrated example, the protrusions 50 extend perpendicular from the longitudinal axis 21. In operation, a user, such as a physician or other medical professional, may grasp the IOL injector 10 with two fingers contacting distal surfaces of the protrusions 50 and the thumb contacting the proximal side of the flange 46. To advance the plunger 18 through the main body portion 12, the storage compartment 14 and the nozzle 16, opposing forces are applied to the protrusions 50 and the flange 46, causing the plunger 18 to advance through the central passage 20, the compartment 24, where the IOL 26 is engaged by the plunger tip 42, and through the passage 28, where the IOL 26 is folded and ultimately expelled from the IOL injector 10 through the opening 34. For example, a user may apply grasp the IOL injector 10 with the index finger and the middle finger contacting distal side surfaces of the protrusions 50 while the thumb contacts the proximal side surface of the flange 46. Opposing forces applied to the index finger and middle finger and the thumb cause the plunger 18 to move distally.

As also shown in FIGS. 1 and 2, the IOL injector 10 includes a door 52. The door 52 includes a hinge 54 that allows the door 52 to pivot into an open position, thereby forming an opening in the compartment 24 of the storage portion 14. The opening provides access to the compartment 24 of the storage portion 14, such as to install thereinto or remove therefrom the IOL 26.

Also shown is a lens stop 56 that is removably coupled to the door 52. In the example shown, the lens stop includes first and second protrusions 58 that are received into apertures 84 (shown, for example, in FIGS. 5 and 6) and a spout 60 received into another aperture 62 formed in the door 52. The protrusion 58 are operable to retain the IOL 26 in a desired position within the compartment 24. For example, the protrusion 58 may be operable to prevent the IOL 26 from moving distally during shipment, storage, or handling. The spout 60 may be used to introduce a viscoelastic material into the compartment 24.

Figure 7:
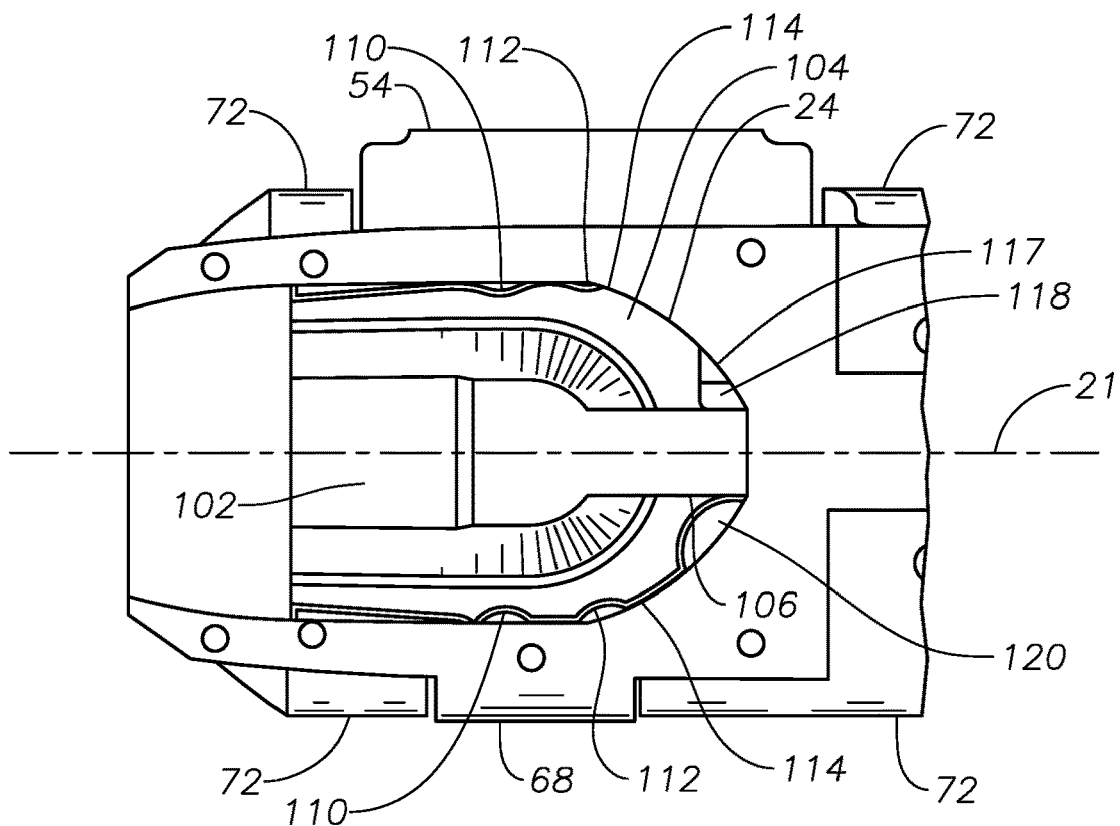
FIG. 7 shows an example compartment formed in an example IOL injector for housing an IOL.

In other implementations, the protrusions 58 may be omitted from the lens stop 56 and, rather, extend through the floor 102, as shown in FIG. 7. In some implementations, the protrusions 58 may be retractable into or from the floor in order to permit delivery of the IOL. Having the protrusions 58 extend from the floor 102 may provide for easier installation of the IOL into the compartment 24 during assembly. That is, with the protrusions 58 extending from the floor, placing the IOL in a desired orientation and/or position may be faster and simpler compared to having the protrusions 58 formed on the lens stop 56. With the protrusions located on the lens stop 56, assembly of the IOL into the compartment 24 may require additional time and effort because, once the IOL is installed into the compartment 24, the door 52 is closed and the lens stop 56 is inserted onto the door 52. The orientation of the IOL injector 10 may need to be carefully monitored so that the IOL does not shift within the compartment 24 prior to insertion of the lens stop 56. This additional monitoring of the IOL injector may require additional time and handling during assembly.

Although FIGS. 1 and 2 show one example IOL injector within the scope of the disclosure (i.e., a manually powered IOL injectors in which a user provides the work needed to advance an IOL through and out of the IOL injector), the scope of the disclosure is not so limited. Rather, the scope of the disclosure encompasses other types of injectors, including other types of manually actuated injectors, automated injectors in which a power source is used to advance the plunger, preloaded IOL injectors, manually loaded IOL injectors, semi-automated injectors, e.g., IOL injectors in which advancement of the IOL is powered by both manually by a user and by a power source, either simultaneously or in series. Thus, while the present disclosure is made in the context of a manually powered IOL injectors, other types of IOL injectors are within the scope of the disclosure.

Figure 3:
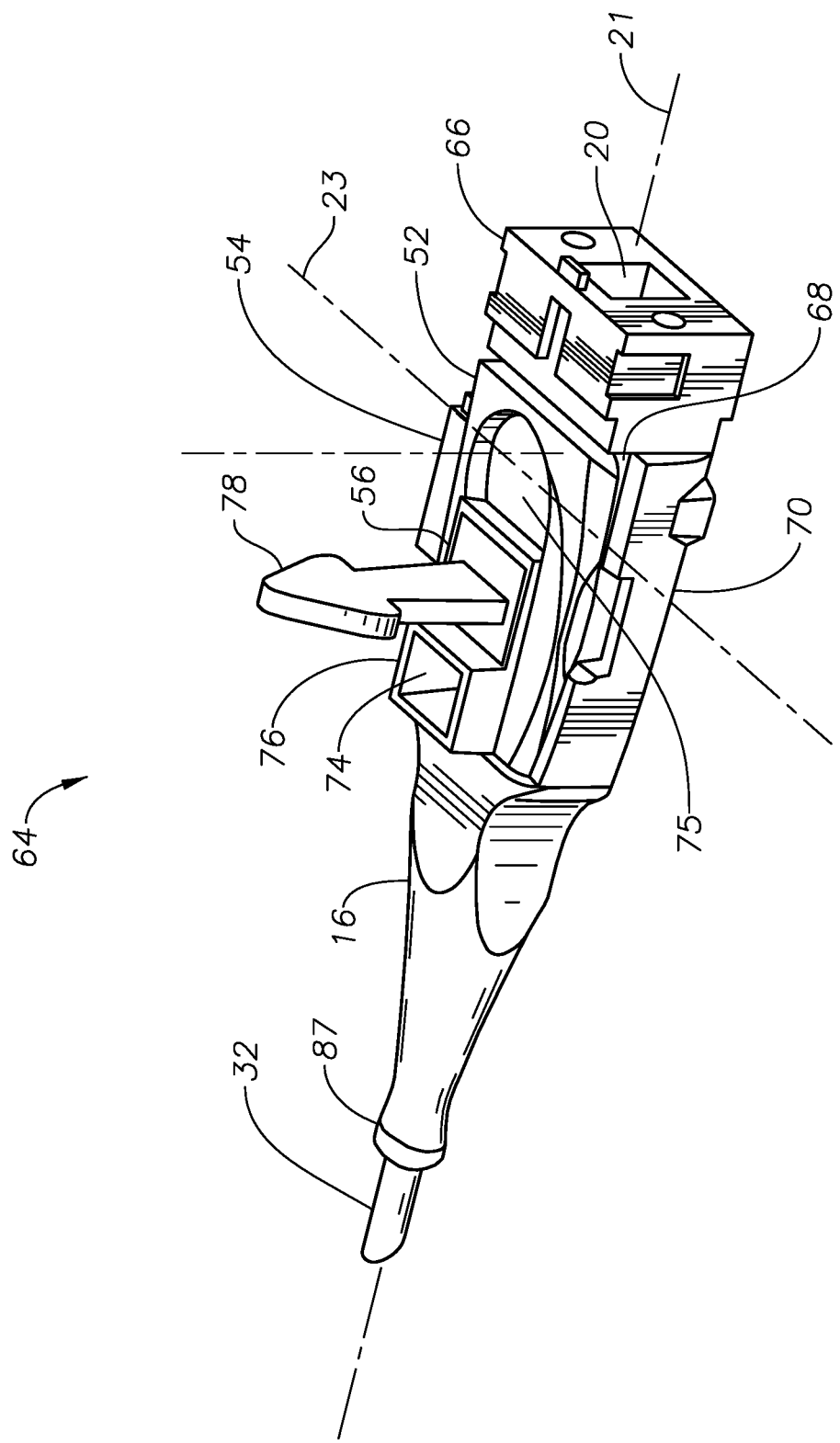
FIG. 3 is a perspective view of a distal portion of an example IOL injector.
Figure 4:
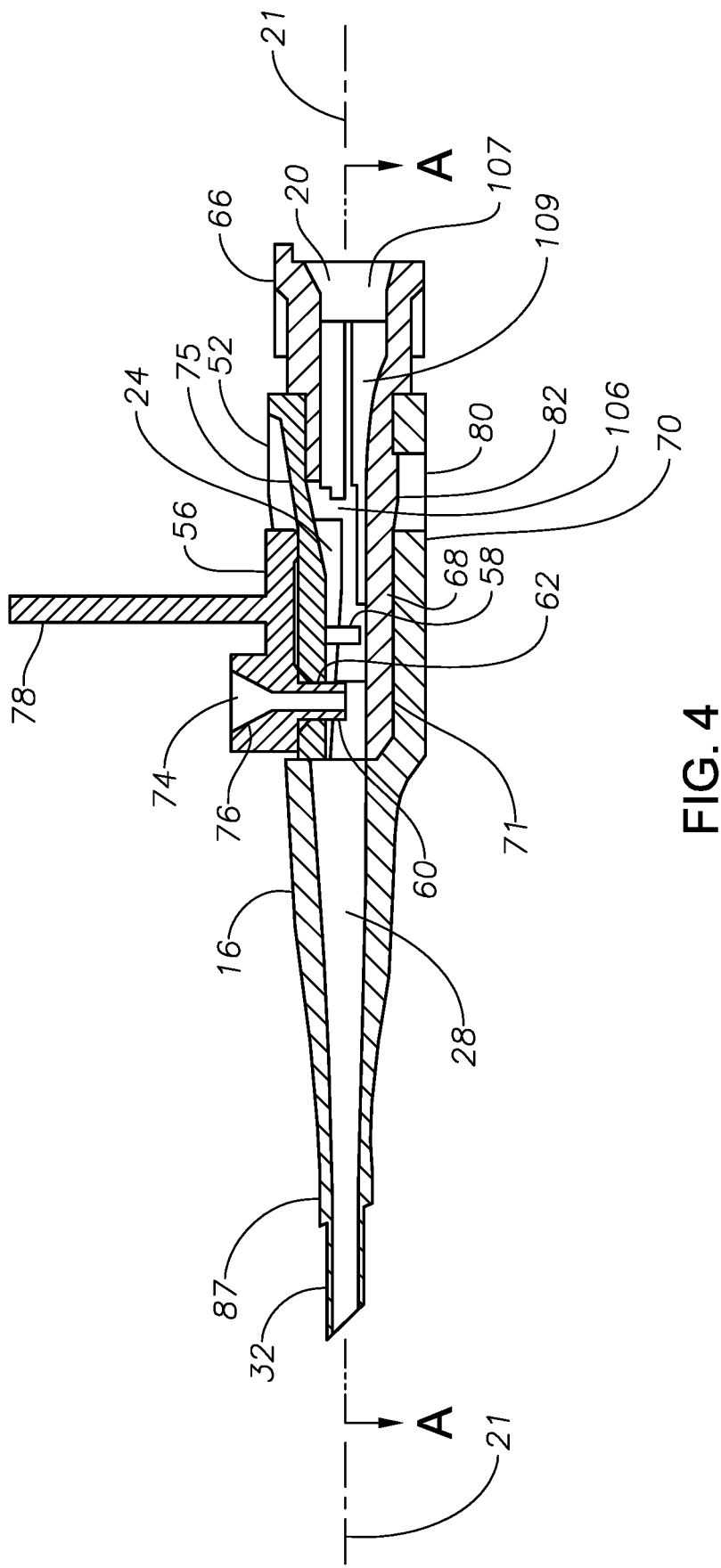
FIG. 4 is a cross-sectional view of the distal portion of the IOL injector shown in FIG. 3.

FIGS. 3 and 4 show an example implementation of distal end portion 64 of an IOL injector, such as IOL injector 10. FIGS. 3 and 4 show the nozzle 16, the storage portion 14, and a distal portion 66. In some instances, the distal portion 66 may be an integral part of the main body portion 12. In other implementations, the distal portion 66 may be a separate component that is coupled to the main body portion 12. As shown in FIG. 3, the door 52 may form an integral part of the storage portion 14 in that the door 52 may be integrally formed with the remainder of the storage portion 14. The hinge 54 may also be integrally formed with the storage portion 14 and define a living hinge.

Figure 10:
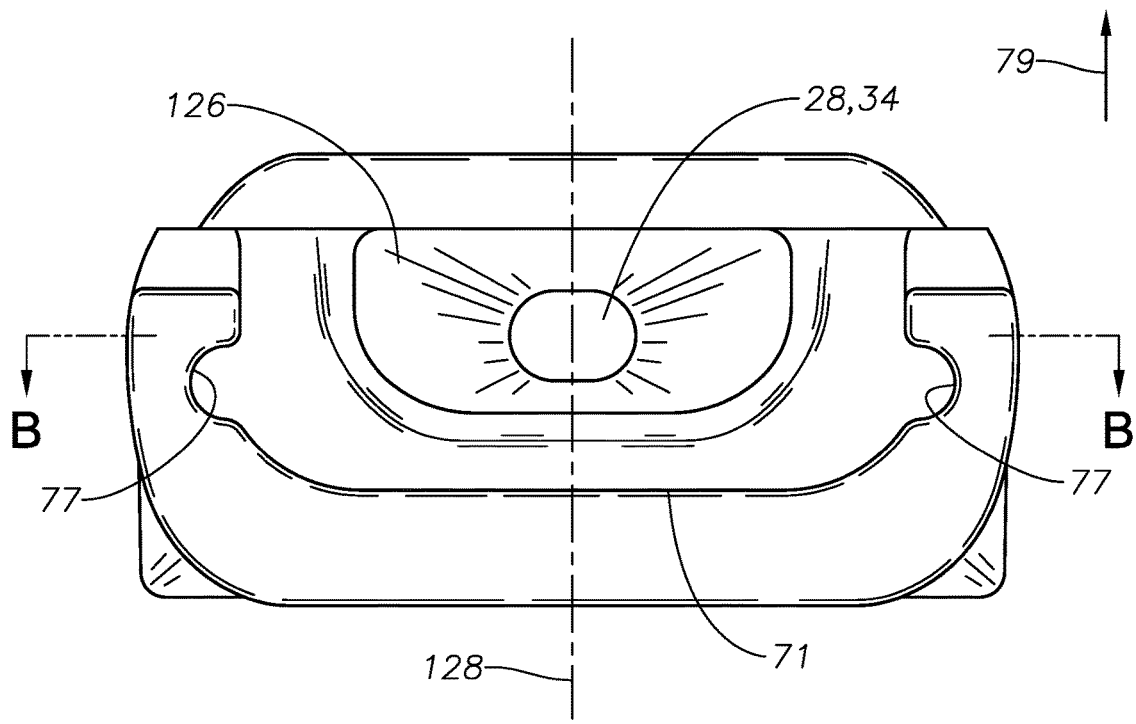
FIGS. 10-13 show various views of an example nozzle.

As shown in the example of FIGS. 3 and 4, the storage portion 14 may be defined by the door 52 and a distally extending portion 68 of the main body portion 12. The nozzle 16 may include a proximal portion 70 that defines a slot 71 that is sized and shaped to receive the distally extending portion 68 of the main body portion 12. As shown in FIG. 7, the distally extending portion 68 may include rails 72 that are received into grooves 74 formed in the proximal portion 70, as shown in FIG. 10. Thus, in some implementations, the main body portion 12, the distally extending portion 68, the door 52, and the hinge 52 may be integrally formed. The door 52 provides access to the compartment 24 and, when the door 52 is opened, permits installation of an IOL, e.g., IOL 26, into the compartment 24. In some instances, the IOL may be loaded prior to delivery to the user, such as during part of a manufacturing process. Thus, in some implementations, the IOL injector 10 may be preloaded with an IOL prior to delivery to a user. In other implementations, the IOL may be loaded into the compartment 24 by a user just prior delivery into a patient by the user. Thus, in some implementations, the IOL injector 10 may be a manually loaded IOL injector, being loaded with an IOL just prior to delivery into a patient.

FIGS. 3 and 4 also show the lens stop 56 coupled to the door 52. As shown, the lens stop 56 may be received in a recess 75 formed in the door 52. The spout 60 defines a passage 74 that has a flared open end 76. The flared open end 76 may receive a needle or other dispensing device used to dispense a viscoelastic into the compartment 24. A protrusion 58 is also shown extending into the compartment 24. The lens stop 56 also includes protrusion 78 extending outwardly. A user may grip the protrusion 78 and pull the lens stop 56 in a direction perpendicular to the longitudinal axis 21 in order to remove the lens stop 56 from the IOL injector 10.

Referring to FIG. 4, the proximal portion 70 of the nozzle 16 includes an aperture 80 that receives a protrusion 82 formed in the distally extending portion 68. The aperture and the protrusion 82 form an interlocking fit to secure the nozzle 82 to the distally extending portion 68. In other implementations, the protrusion 82 and aperture 80 may be omitted, and the nozzle 16 and the distally extending portion 68 may be joined in another way, such as, for example, an adhesive, a friction fit, a fastener, some other interlocking feature, or in any other manner operable to join the nozzle 16 to the distally extending portion 68. Thus, the connection between the nozzle 16 and the distally extending portion 68 represents one example way of coupling the nozzle 16 and the distally extending portion 68.

As shown in FIG. 4, the distal tip 32 of the nozzle 16 may be beveled so as to form an oblique angle with the longitudinal axis 21. The nozzle 16 also includes a depth guard 847. The depth guard 874 operates to limit an amount by which the distal tip 32 may be received into the eye, such as while delivering an IOL from the IOL injector 10. For example, in use, the depth guard 874 abuts an exterior surface of the eye in order to limit an amount by which the distal tip 32 of the nozzle 16 may be inserted into an incision formed in the eye.

Figure 5:
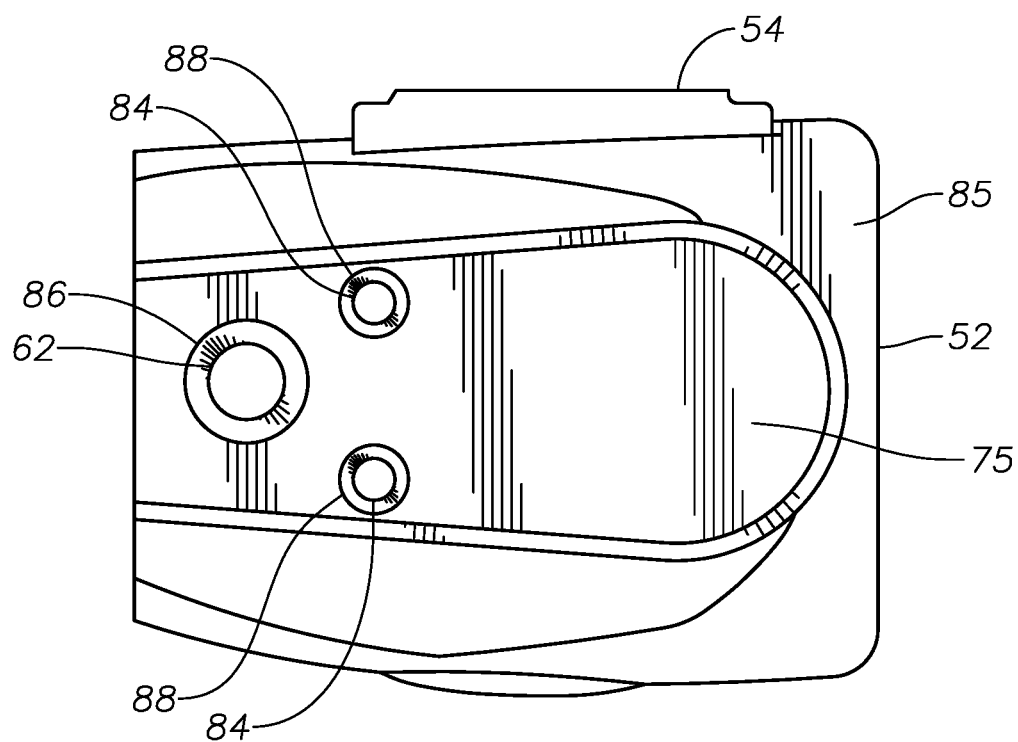
FIG. 5 shows an interior surface of an example door of an example IOL injector.
Figure 6:
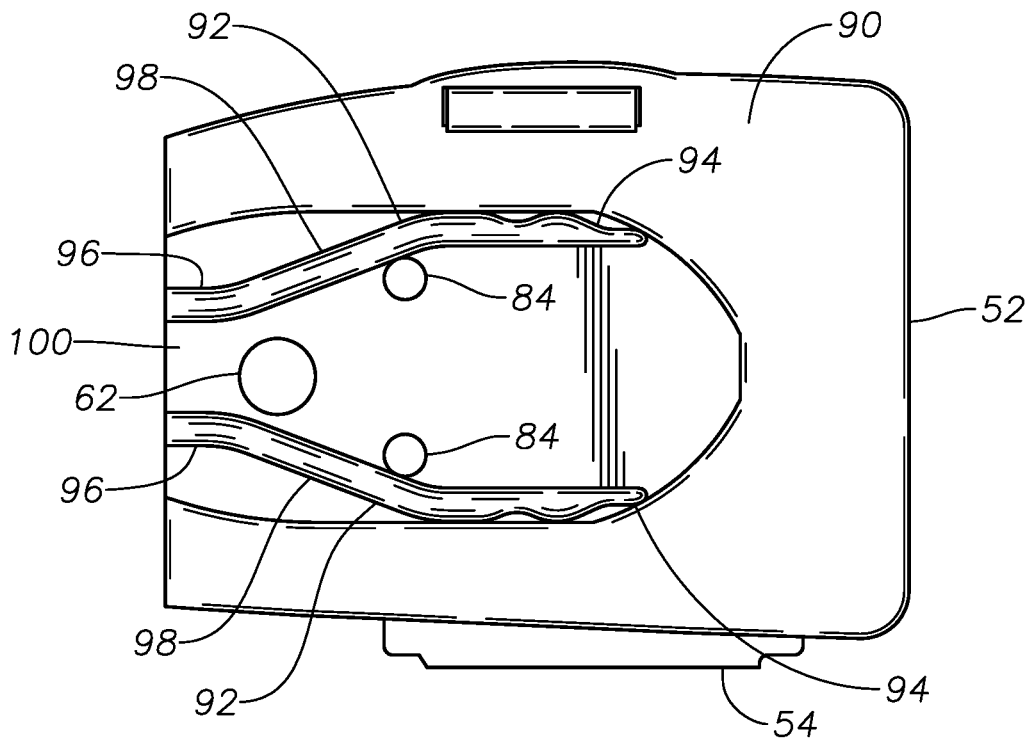
FIG. 6 shows an exterior surface of the door shown in FIG. 5.

FIGS. 5 and 6 show top and bottom views, respectively, of the door 52. In the example shown, the door 52 includes two apertures 84 which receive the protrusions 58 of the lens stop 56. While two protrusions 58 are shown, the scope of the disclosure is not so limited. Rather, additional or fewer protrusions 58 may be used, resulting a corresponding additional or fewer apertures 84. In the illustrated example, two apertures 84 are provided and disposed symmetrically about the longitudinal axis 21 of the IOL injector 10. The symmetrical placement of the apertures 84 and protrusions 58 provide for a symmetrical geometry and balanced loading imposed on the IOL disposed in the compartment 24 when the IOL 26 contacts the protrusion 58. Aperture 62 is also shown. As explained above, the aperture 62 receives the spout 60 used to deliver viscoelastic material into the compartment 24. FIG. 5 shows an exterior surface 85 of the door 52 and shows that the outer openings 86 of the aperture 62 and the outer openings 88 of the apertures 84 are flared to assist in installation of the lens stop 56 to the door 52.

FIG. 6 shows an interior surface 90 of the door 54. Rails 92 are formed on the internal surface 90 and extend into the compartment 24. The rails 92 function to ensure that the vertical position of the IOL 26 remains constant during advancement of the IOL 26 during delivery. That is, the rails 92 prevent the IOL 26 from moving towards or away from the door 52 during advancement of the IOL 26. The rails 92 are arranged symmetrically relative to the longitudinal axis 21. As a result, the rails 92 provide balanced loading to the IOL 26 during advancement of the IOL 26. As a result, the rails 92 are configured to maintain the IOL 26 in a desired orientation during advancement and delivery. Particularly, the symmetrical configuration of rails 92 assists in avoiding undesired rotation of the IOL 26 about a vertical axis 25, a lateral axis 23, or the longitudinal axis 21 during advancement.

As also shown in FIG. 6, each of the rails 92 includes a proximal portion 94, a distal portion 96, and a converging portion 98. Thus, along the length of the rails 92 in the distal direction, the rails 92 converge to define a narrowed slot 100. The slot 100 assists in maintaining a path of travel of the plunger rod 40 as the plunger rod 40 advances the IOL 26 through compartment 24 and the passage 28.

FIG. 7 shows a top view of the distally extending portion 68 and the compartment 24 formed therein. Within the compartment 24, the distally extending portion 68 defines a floor 102 and a raised shelf 104 that is vertically displaced from the floor 102 along the vertical axis 25. The raised shelf 104 supports the IOL 26 when the IOL 26 is a storage condition. That is, the IOL 26 rests upon the raised shelf 104 during storage with the IOL 26 in an unstressed condition. The raised shelf 104 is divided by a groove 106. The floor 102 extends along the groove 106 and provides a path for the plunger rod 40 as the plunger rod 40 is advanced through the compartment 24. A sloped walls 108 extend between the floor 102 and the raised shelf 104, and vertical walls 108 extend between the raised shelf 104 and the floor 102 along the groove 106. In some implementations, the walls 108 may be considered substantially vertical due to a minor angle imparted thereto for the purposes of draft during manufacturing. The angle of these wall 108 relative to the floor 102 is, therefore, minor of only a few degrees to account for mold design where the distally extending portion 68 is an injection molded part, for example.

The features of the distally extending portion 68 forming the compartment 24 are symmetrically arranged to provide both symmetrical loading to the IOL 26 during advancement of the IOL 26 during delivery. For example, protuberances 110 and 112 are formed along opposing walls 114. In the illustrated example, the shapes of the protuberances 110 and 112 are different between the opposing walls 114. However, locations where the protuberances 110 and 112 contact the IOL 26 along a perimeter 116 of the IOL 26 are symmetrical about the longitudinal axis 21, as shown, for example, in FIG. 8. The protuberances 110 and 112 operate to define an at-rest or storage position of the IOL 26 during shipment or storage during which time the IOL 26 remains unstressed. The protuberances 110 and 112 work together to define a recess within the compartment 24 in which the IOL 26 resides prior to being advanced by the plunger 18. Thus, the loading experienced by the IOL 26 from the protuberances 110 and 112 during both storage and during advancement is symmetrical, tending to keep the IOL 26 from rotating, e.g., about a vertical axis coming out of the page in FIGS. 7 and 8, during advancement. In other implementations, shapes of the protuberances 110 and 112 disposed along one of the walls 114 may be the same as the shapes of the corresponding protuberances 110 and 112 formed on the opposing wall 114

Figure 8:
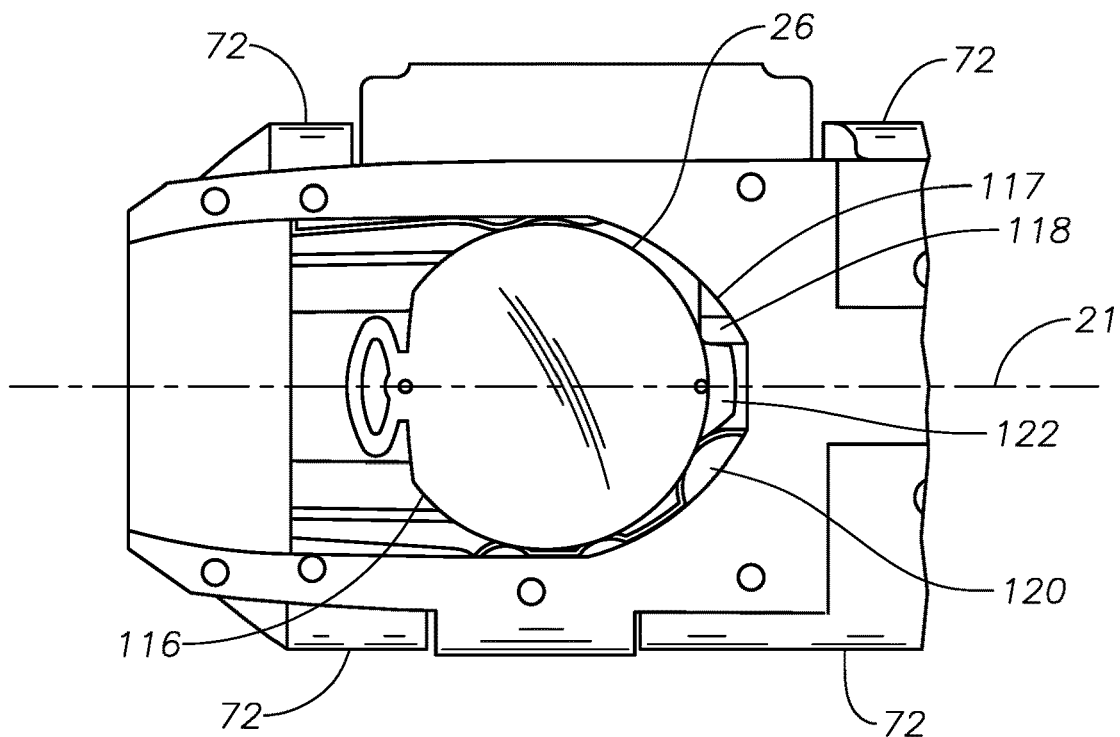
FIG. 8 shows the compartment of FIG. 7 with an example IOL disposed therein.

In the example shown in FIGS. 7 and 8, a proximal end 117 of the compartment 24 includes unsymmetrical features 118 and 120. In the example, shown, the features 118 and 120 are raised steps that extend from the raised shelf 104. In other implementations, the features 118 and 120 may be in the form of other topographical features integral to the distally extending portion 68 or may be other components, recesses, voids, combinations thereof, or other arrangement that operate to permit loading of the IOL 26 in a defined orientation. The features 118 and 120 conform to a nonsymmetrical tab 122 formed on the IOL 26. For example, in the illustrated example, a first side of the tab 122 may be flat and aligned with the longitudinal axis 21, while a second side of the tab 122 may be curved.

Thus, in the illustrated example, the features 118 and 120 cooperate to permit the IOL 26 from being inserted into the compartment 24 in only one orientation. That is, if the IOL 26 shown in FIG. 8 were flipped over such that the optical surface of the IOL 26 shown in FIG. 8 were now was facing the opposite direction, the shape of the tab 122 would longer conform to the shapes of the features 118 and 120. As a result, the IOL 26 would no longer rest properly in a desired orientation.

While FIGS. 7 and 8 show an implementation in which the proximal end 117 includes unsymmetrical features, other implementations may omit features 118 and 120 or, in still other implementations, include features 118 and 120 that are symmetrical or symmetrically engage the IOL 26.

The IOL 26 shown in FIGS. 7 and 8 may be an optic portion of a two-piece IOL. A second piece of the two-piece IOL may be in the form of a ring-shaped base. While not shown in the figures, the ring or base may be delivered with the use of an IOL injector that is similar to the examples described herein. In still other implementations, single-piece IOLs may also be delivered using the example IOL injectors described herein.

Figure 9:
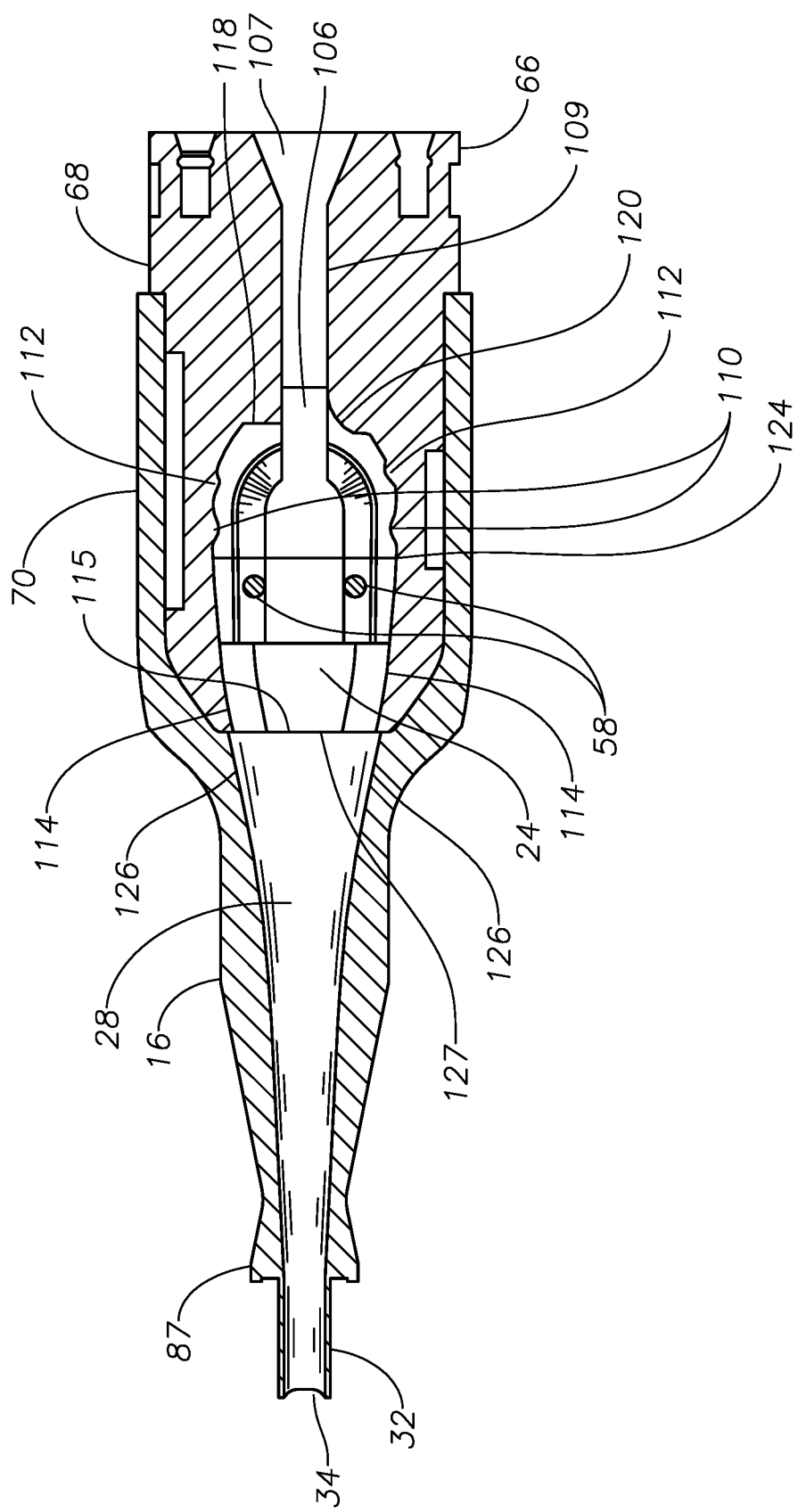
FIG. 9 is a cross-sectional view of the distal portion of FIG. 3.

FIG. 9 is a longitudinal cross-sectional view taken along line AA shown in FIG. 4. The line AA is disposed along the longitudinal axis 21. As shown in the example shown in FIG. 9, the walls 114 of the compartment 24 extending distally from line 124 are symmetrically arranged relative to the longitudinal axis 21. These walls 114 converge, narrowing the compartment 24 in the distal direction. Although FIG. 9 shows that portions of the compartment 24 extending proximally from line 124 are not symmetrical, in other implementations the entirety of the compartment 124 may be symmetrical about the longitudinal axis 21. For example, the features 118 and 120 are shown as being unsymmetrical. However, in other implementations, the features 118 and 120 may be omitted or formed so as to be symmetrical about the longitudinal axis. Similarly, the protuberances 110 and 112 are also shown to be slightly unsymmetrical. Again, though, as explained above, the protuberances 110 and 112 contact the perimeter 116 of the IOL 26 symmetrically although their respective shapes are not shown as being symmetrical about longitudinal axis 21. In other implementations, though, the protuberances 110 and 112 may be symmetrically formed about the longitudinal axis 21.

A wall 126 of the nozzle 16 that define passage 28 is also symmetrically arranged relative to the longitudinal axis 21 and form a continuous contour with the walls 114 of the compartment 24. The wall 126 is smooth and continuous, which results in the passage 28 being continuous and smooth. Consequently, a distal opening 115 of the compartment 24 corresponds to the proximal opening 127 of the passage 16. Moreover, as shown in FIG. 10, the passage 28 is symmetrical about a vertical plane 128. The symmetrical nature of the compartment 24 and the passage 28 operate fold the IOL 26 while maintaining symmetrical and even loading to the IOL 26 during folding. This symmetrical and even loading applied to the IOL 26 prevents or substantially reduces rotation of the IOL about any of the vertical, horizontal, or longitudinal axes 25, 23, and 21, respectively.

FIG. 9 also shows the groove 106. The groove 106 that defines a path of travel for the plunger rod 40 as the plunger 18 is advanced extends proximally through the distally extending portion 68, defining a passage 109. In the illustrated example, the passage 109 has a tapered distal end 107 that laterally narrows in the distal direction. The tapered distal end 107 may also narrow in the vertical direction, as shown in FIG. 4. As a result, the passage 109 and groove 106 may confine the plunger tip 40 and define a path of travel thereby.

In operation, as the plunger 18 is advanced, the plunger rod 40 passes through the central passage 20, through the passage 109, and then the groove 106. As the plunger 18 continues to advance, the plunger tip 42 engages the IOL contained within the compartment 24. For example, the plunger tip 42 may engage the tab 122 of the IOL 26 and advance the IOL 26 through the compartment 24. As the compartment 24 narrows in the distal direction, such as due to convergence of walls 114 of the compartment 24, the perimeter 116 of the IOL 26 may begin to engage each of the walls 114. The IOL 26 engages the walls 114 at essentially the same time, causing balanced loading to be applied to the IOL 26 about the plane passing through the longitudinal axis 21 and vertical axis 25 (interchangeably referred to as the "Vertical Plane").

In the implementations where the perimeter 116 of the IOL 26 does engage the walls 114, the opposing sides of the IOL 26, as referenced relative to the Vertical Plane, begin to move in the direction of arrow 79 (shown in FIG. 10), as the IOL 26 begins to fold. The rails 92 formed on the door 52 prevent the IOL from lifting in the direction of arrow 79 or pivoting about the lateral axis 23, thereby maintaining a position of the IOL 26 within the compartment 24. As advancement of the IOL 26 continues in the distal direction, the lateral sides of the IOL 26 engage the wall 126 of the nozzle 16 that defines the passage 28. As the passage 28 continues to narrow, the wall 126 further folds the lateral sides of the IOL 26 until, eventually, the IOL 26 is fully folded into a cylindrical form. As the plunger 18 continues to move distally, the folded IOL 26 is eventually expelled from the opening 34 formed in the distal tip 32 of the nozzle 16.

As explained above, in some implementations, the walls 114 of the compartment 24 may engage the IOL 26 to initiate folding of the IOL 26. In other implementations, the walls 114 may begin folding the IOL 26. Rather, in some implementations, the wall 126 of the nozzle 16 may exclusively cause the IOL 26 to fold.

Figure 11:
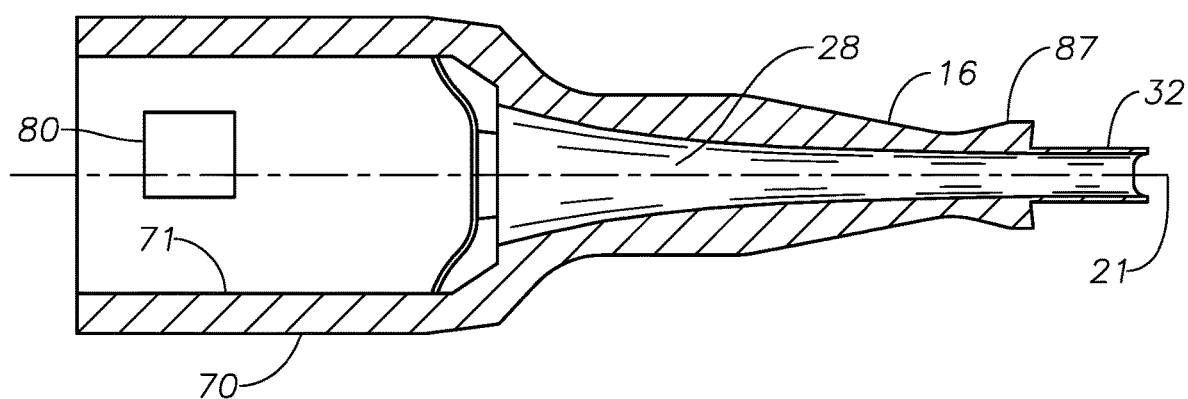
Figure 13:
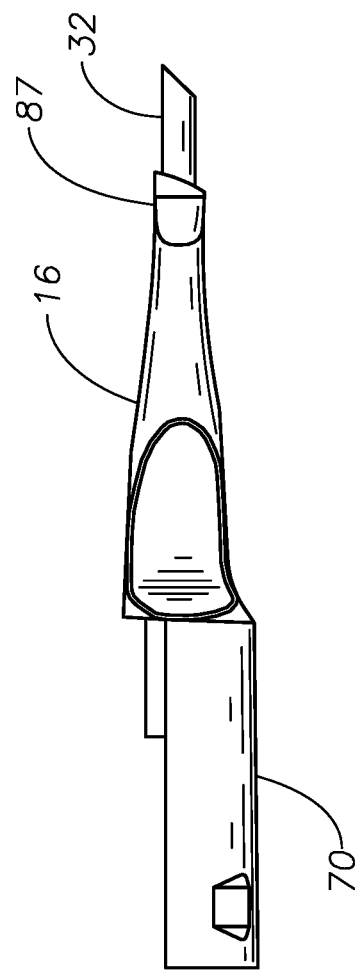

FIG. 11 shows a cross-sectional view of the nozzle taken along line BB. Once again, the passage 28 is shown as being symmetrical about the passage 28 is symmetrical about a vertical plane passing through both longitudinal axis 21 and vertical axis 25 (shown in FIG. 3). As such, the bore 28 omits the inclusion of any asymmetrical features disposed within the passage 28, such as features formed in one portion of wall 126 and not mirrored on a counterpart portion of wall 126 about the plane of symmetry, i.e., the plane extending through longitudinal axis 21 and vertical axis 25.

Figure 12:
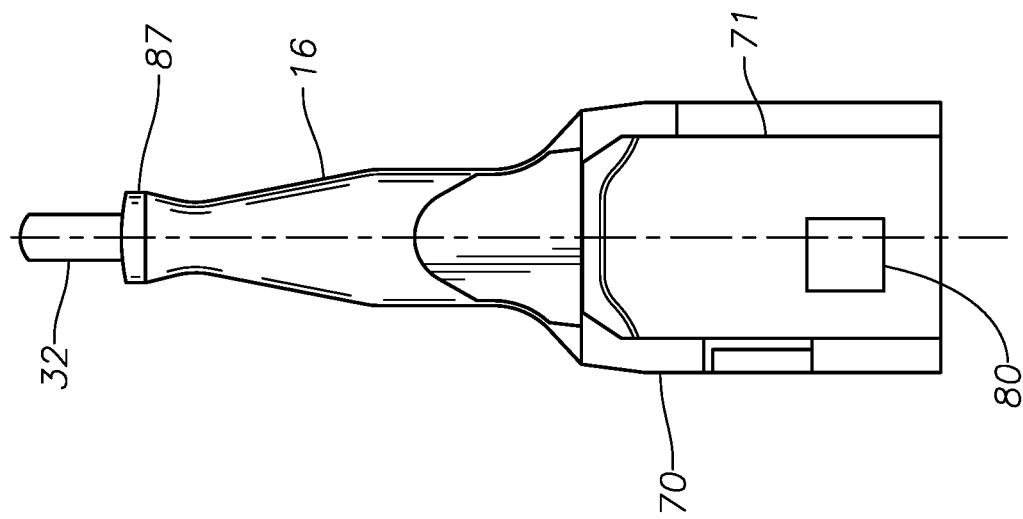

Also shown in FIG. 11 is the aperture 80. The aperture 80 is shown laterally offset from the longitudinal axis 21. In other implementations, the aperture 80 may be aligned with longitudinal axis 21. Further, the aperture 80 is shown as being square. In other implementations, the aperture 80 may be rectangular, circular, triangular, or have any other desired shape. In such implementations, the corresponding protrusion 82 may have a shape corresponding to the aperture 80. In other implementations, the shape of the protrusion 82 may not correspond to the aperture 80, but the aperture 80 and protrusion 82 are still operable to couple the nozzle 16 to the distally extending portion 68. FIG. 12 shows a top view of the nozzle 16 showing the proximal portion 70 that defines the slot 71 into which the distally extending portion 68 is received and the aperture 80. FIG. 11 shows a side view of the nozzle 16.

Figure 14:
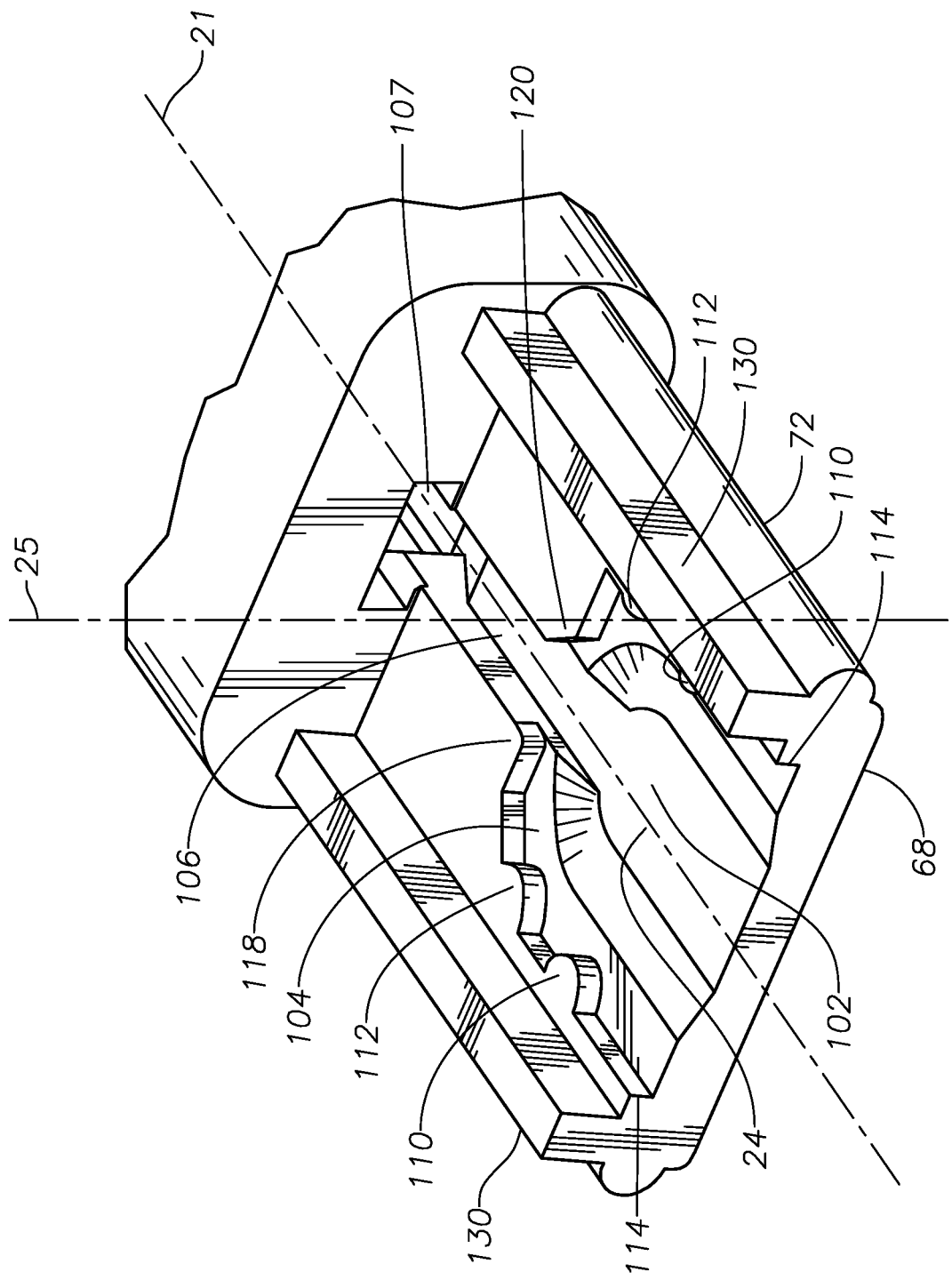
FIG. 14 is a perspective view of an example distally extending portion of an IOL injector that shows an example compartment adapted for storing an IOL.

FIG. 14 shows another example implementation of the distally extending portion 68. As mentioned above, the distally extending portion 68 may be integral to a main body portion of an IOL injector, e.g., main body portion 12 of IOL injector 10. In other implementations, the distally extending portion 68 may be a separate component that is coupled to the main body portion of an IOL injector or another part thereof. The distally extending portion 68 shown in FIG. 14 and the corresponding nozzle 16 shown in FIGS. 15 and 16 (discussed in more detail below) are generally applicable to the pre-loaded variety of IOL injectors, i.e., IOL injectors in which the IOL is preloaded by the manufacturer prior to delivery to the user. However, the distally extending portion 68 and corresponding nozzle 16 may be of the manually loaded variety in which a user loads the IOL prior to delivery into a patient. The distally extending portion 68 may be similar to that shown in FIGS. 7 and 8, and, while many of the features of the distally extending portion 68 shown in FIG. 14 are identified, the aforementioned description of those features are applicable here and will not be repeated.

As shown in FIG. 14, the distally extending portion 68 defines a compartment 24 in which an IOL may be stored prior to delivery. As explained above, the compartment 24 is symmetrical about a vertical plane passing through the longitudinal axis 21 and the vertical axis 25. The distally extending portion 68 also includes longitudinally extending walls 130 with rails 132. The rails 132 are received in slots 134 formed in a proximal portion 70 of the nozzle 16, as shown in FIG. 15.

Figure 15:
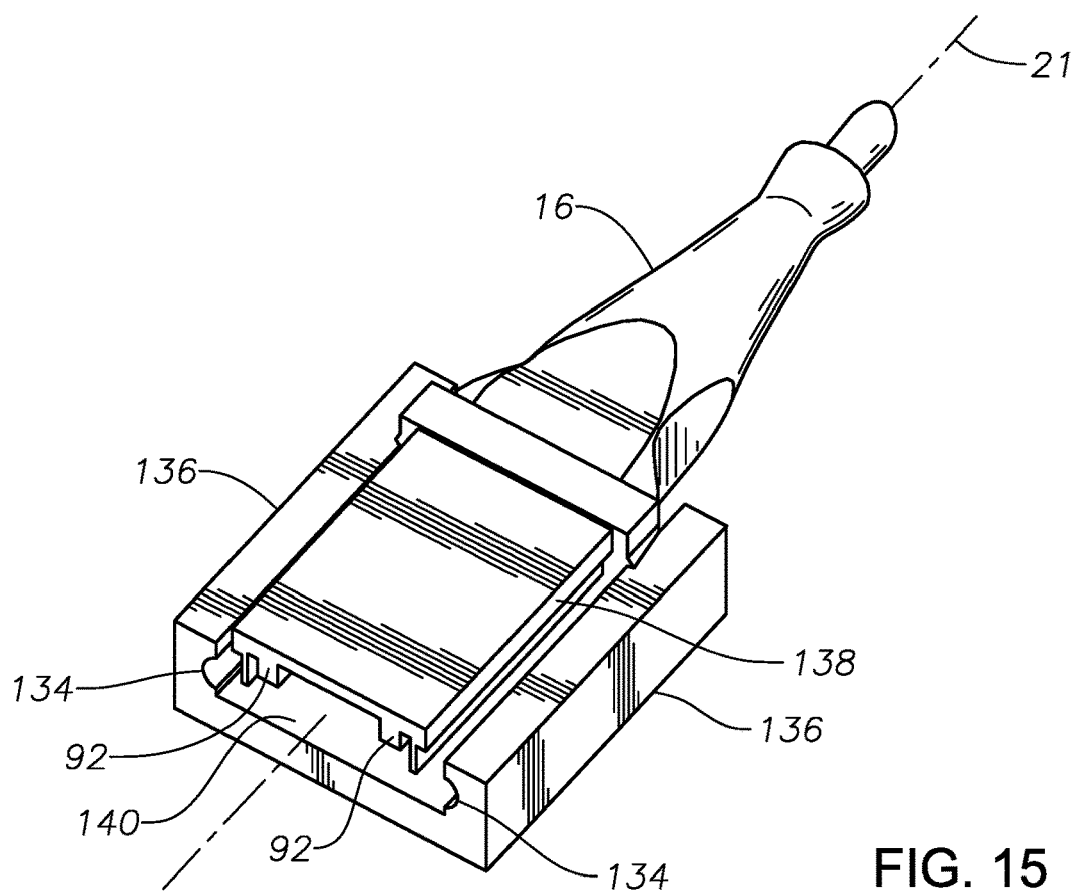
FIGS. 15 and 16 show another example nozzle adapted to receive the distally extending portion shown in FIG. 14.

Referring to FIG. 15, the nozzle 16 includes the proximal portion 70 that includes longitudinally extending walls 136 and a cover 138 that define a cavity 140 into which the distally extending portion 68 is received. When the distally extending portion 68 is received into the cavity 140, the rails 72 are received into slots 134, and the longitudinally extending walls 130 reside adjacent to an inboard of the longitudinally extending walls 136 of the proximal portion 70 of the nozzle 16. Further, cover 138 encloses the compartment 24. Because cover 138 is fixed relative to the remainder of the nozzle 16, access to the compartment 24 via the cover 138 is not possible when the distally extending portion 68 is received into the nozzle 16. The cover includes rails 92 which may be similar to the rails 92 explained above in the context of FIG. 6. Although the rails 92 are not shown in FIG. 16 as having the inwardly converging shape as those shown in FIG. 6, it is within the scope of the present disclosure that the rails 92 shown in FIG. 16 have a similar shape, i.e., having a proximal portion, a distal portion, and a converging portion, as described above. The cover 138 also includes walls 142 extending therefrom. The walls are inwardly offset from the longitudinally extending walls 136.

Figure 16:
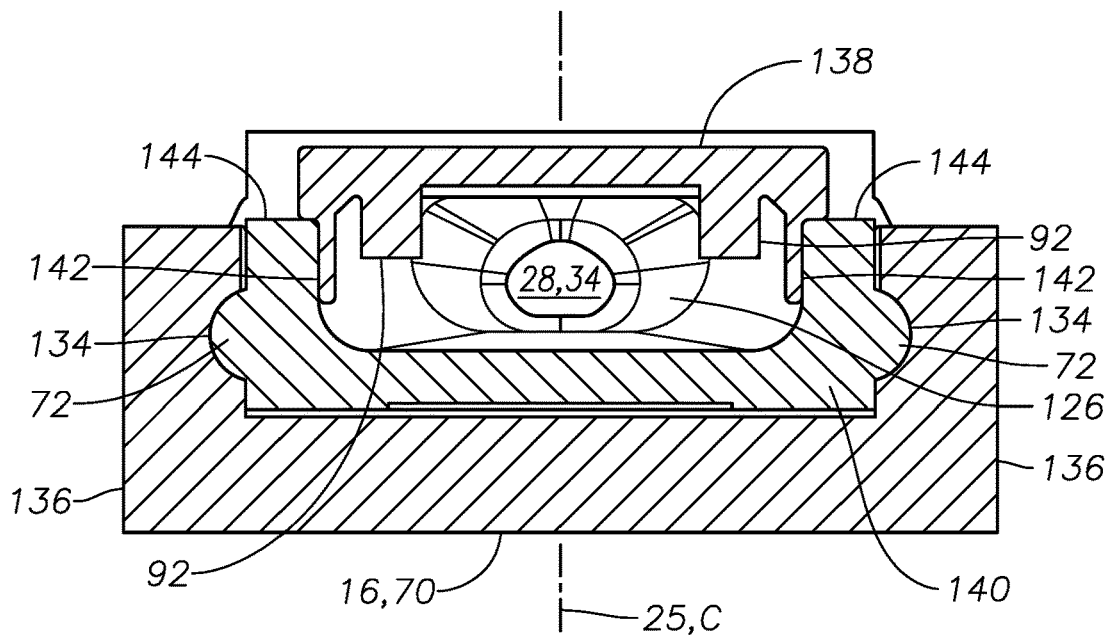

FIG. 16 shows a back end view of the nozzle 16 and includes dashed lines 144 that identify locations of the distally extending walls 130 of the distally extending portion 68 when received into the cavity 140 of the nozzle 16. Thus, each of the distally extending walls 130 of the distally extending portion 68 is disposed between a distally extending wall 136 and wall 142 of the nozzle 16. As also shown in FIG. 16, the passage 28 is symmetrical about a plane passing through vertical axis 25 and the longitudinal axis 21, identified as plane C in FIG. 16. Similar to the example shown in FIG. 9, above, the walls 114 of the compartment 24 and the wall 126 of the nozzle 16 defining the passage 28 form a continuous contour that provides for even loading to the IOL as the IOL is advanced through the compartment 24 and passage 28 and is folded therein. As a result, the IOL avoids being rotated about vertical, longitudinal, or lateral axes, while the rails 92 maintain a horizontal position of the IOL during advancement by the plunger.

The example nozzle 16 and distally extending portion 68 shown in FIGS. 14-16 may reduce assembly time of the associated IOL injector and IOL therein as well as reduce the risk of contamination or damage to the IOL in the case of a preloaded IOL injector. During assembly, the IOL may be placed in the compartment 24 of the distally extending portion 68 shown in FIG. 14. Once the nozzle 16 is coupled thereto, access to the IOL within the compartment 24 is not possible due to the cover 138 being fixed to the nozzle 16. Thus, in use, the user, e.g., a surgeon or nurse, is not able to access the IOL because the compartment 24 fully enclosed and the position of the cover 138 is fixed. Thus, such an implementation may provide for improved assembly along with a reduced risk of damage or contamination to the IOL.

FIGS. 17-22 show example plunger tips 42. While the example plunger tips 42 have different end shapes, the plunger tips 42 are symmetrical about the vertical axis 25. FIGS. 17 and 18 show an example plunger tip 42 that flat end face 146. The flat end face 146 may be parallel with a plane passing through the vertical axis 25 and lateral axis 23. The plunger tip 42 shown in FIGS. 19 and 20 has a "V"-shape in which a first planar surface 148 and a second planar surface 150 intersect at an edge 152. In the example shown, the edge 152 may be centered vertically along the plunger tip 42. In other implementations, the edge 152 may be offset vertically from the center of the plunger tip 42. The plunger tip 42 shown in FIGS. 21 and 22 has a concave surface 154. The degree of curvature of the concave surface 154 may be varied such that, in profile, as shown in FIG. 22, the concave surface 154 may define a circular arc, an elliptical arc, a parabolic arc, or some other curved surface. The symmetrical nature of the tips 42 shown in FIGS. 17-22 about the vertical axis 25 also promotes even loading applied to the IOL during advancement and folding, thereby avoiding undesired rotation about the longitudinal, vertical, and lateral axes.

Although the disclosure provides numerous examples, the scope of the present disclosure is not so limited. Rather, a wide range of modification, change, and substitution is contemplated in the foregoing disclosure. It is understood that such variations may be made to the foregoing without departing from the scope of the present disclosure.

What is claimed is:

1. An intraocular lens injector comprising:
   a main body portion defining a central longitudinal axis;
   a storage portion disposed at a distal end of the main body portion, the storage portion comprising a compartment that includes a floor, the compartment adapted to store an intraocular lens prior to delivery, the compartment shaped symmetrically about a plane extending through the central longitudinal axis and a vertical axis extending perpendicular to the floor of the compartment such that the compartment applies balanced loading to the intraocular lens relative to the plane;
   a door that overlays the compartment, wherein the door comprises rails formed on an inner surface and symmetrically disposed relative to the plane;
   a lens stop removably attachable to the door, the lens stop comprising:
      protrusions extending from a first surface adapted to abut an exterior surface of the door, opposite an interior surface of the door,
      wherein the door further comprises first apertures extending therethrough, the first apertures arranged symmetrically relative to the plane, and wherein the protrusions extend through the first apertures formed in the door, the protrusions operable to symmetrically contact the intraocular lens disposed in the compartment and limit movement of the intraocular lens therein;
   a nozzle disposed at a distal end of the storage portion, the nozzle comprising:
      an interior wall defining a passage, the interior wall and passage symmetrical about the plane;
      a distally extending distal tip; and
      an opening formed at a distal end of the distally extending distal tip, the opening in fluid communication with the passage; and
   a plunger received into the main body portion and slideable therein, the plunger comprising a plunger tip that is symmetrical about the plane.

2. The intraocular lens injector of claim 1, wherein the compartment comprises walls symmetrically disposed about the plane, wherein the walls of the compartment and the interior wall of nozzle define a continuous contour.

3. The intraocular lens injector of claim 1, wherein the compartment comprises a distal opening, wherein the nozzle comprises a proximal opening, and wherein the distal opening and the proximal opening correspond to each other.

4. The intraocular lens injector of claim 3, wherein the walls of the compartment converge such that the distal opening is narrower than a proximal portion of the compartment.

5. The intraocular lens injector of claim 1, wherein the compartment comprises walls symmetrically disposed about the plane, wherein the compartment comprises protuberances formed along the walls, and wherein the protuberances are adapted to contact the intraocular lens disposed in the compartment at locations that are symmetrical about the plane.

6. The intraocular lens injector of claim 1, wherein each of the rails comprises an inwardly converging portion that are symmetrically arranged relative to the plane.

7. The intraocular lens injector of claim 6, wherein the plunger comprises a plunger rod, the plunger tip disposed at a distal end of the plunger rod and wherein the rails converge to define a slot adapted to maintain a path of travel of the plunger rod.

8. The intraocular lens injector of claim 1, wherein the lens stop further comprises an additional aperture, the additional aperture centrally located along the plane, wherein the lens stop further comprises a spout defining a passage, and wherein the spout is received into the additional aperture when the lens stop is attached to the door.

9. The intraocular lens injector of claim 1, wherein the protrusions extend from the floor, the protrusions being arranged symmetrically relative to the plane, and wherein the protrusions are operable to symmetrically contact the intraocular lens disposed in the compartment and limit movement of the intraocular lens therein.

10. The intraocular lens injector of claim 9, wherein the first protrusions are retractable.

11. The intraocular lens injector of claim 1, wherein the nozzle comprises a proximal portion, the proximal portion comprising:
   longitudinally extending sidewalls; and
   a cover, the cover and the longitudinally extending sidewalls defining a cavity,
   wherein the storage portion is receivable into the cavity, the cover and the longitudinally extending sidewalls enclosing the compartment.

12. The intraocular lens injector of claim 11, wherein the cover is fixedly attached to the nozzle.

13. The intraocular lens injector of claim 12, wherein the storage portion comprises longitudinally extending wall and rails extending from the longitudinally extending walls, wherein the longitudinally extending walls of the proximal portion comprise slots formed therein, and wherein the rails are received into the slot when the nozzle is coupled to the storage portion.

14. The intraocular lens injector of claim 12, wherein the cover comprises inner walls, wherein each of the longitudinally extending walls of the storage portion is disposed between one of the longitudinally extending wall of the proximal portion and one of the inner walls of the cover when the storage compartment is coupled to the nozzle.

\* \* \* \* \*